US 009789515B2

(12) United States Patent
Hajati

(10) Patent No.: US 9,789,515 B2
(45) Date of Patent: Oct. 17, 2017

(54) PIEZOELECTRIC TRANSDUCER DEVICE WITH LENS STRUCTURES

(71) Applicant: Arman Hajati, Santa Clara, CA (US)

(72) Inventor: Arman Hajati, Santa Clara, CA (US)

(73) Assignee: FUJIFILM DIMATIX, INC., Lebanon, NH (US)

( * ) Notice: Subject to any disclaimer, the term of this patent is extended or adjusted under 35 U.S.C. 154(b) by 286 days.

(21) Appl. No.: 14/292,445

(22) Filed: May 30, 2014

(65) Prior Publication Data

US 2015/0343492 A1 Dec. 3, 2015

(51) Int. Cl.
*G01N 29/24* (2006.01)
*A61B 8/12* (2006.01)
(Continued)

(52) U.S. Cl.
CPC .......... *B06B 1/0622* (2013.01); *B06B 1/0633* (2013.01); *G01D 5/12* (2013.01);
(Continued)

(58) Field of Classification Search
CPC ....... B06B 1/0622; B06B 1/0633; B06B 1/06; B06B 1/00; G01D 5/12; G01N 29/221; G01N 29/34; G01N 29/2437; G01N 29/2456; G01N 2291/101; G01N 2291/106; G01N 29/26; G10K 11/30; H01L 41/00; B81C 1/00; A61B 8/12; A61B 8/4281
(Continued)

(56) References Cited

U.S. PATENT DOCUMENTS 3,587,561 A * 6/1971 Ziedonis .................. A61B 8/04
310/335
5,134,988 A * 8/1992 Pell ..................... A61B 17/2251
310/334

(Continued)

FOREIGN PATENT DOCUMENTS

EP 2685255 1/2014
EP 2685255 A2 * 1/2014 ......... G01N 29/2406

OTHER PUBLICATIONS

Gobin, "Maxim, Medical imaging, Ultrasound imaging systems, www.maxim-ic.com/medical; last accessed May 30, 2014, http://www.scribd.com/doc/201688798/Ultrasound", (Jan. 23, 2014), pp. 63-78.

(Continued)

*Primary Examiner* — Laura Martin
*Assistant Examiner* — Rose M Miller
(74) *Attorney, Agent, or Firm* — Blakely, Sokoloff, Taylor & Zafman LLP

(57) ABSTRACT

In an embodiment, a probe device includes a portion having a curved surface and a plurality of tiles variously coupled to the curved surface. The tiles each include a plurality of piezoelectric transducer elements and a base adjoining and supporting the plurality of piezoelectric transducer elements. The probe device further comprises curved lens portions each coupled to a respective one of the plurality of tiles, wherein for each of the tiles, the plurality of piezoelectric transducer elements of the tile are to propagate a wave toward the respective curved lens portion. In another embodiment, the probe device further comprises a sheath material surrounding the curved lens portions.

11 Claims, 12 Drawing Sheets

(51) Int. Cl.
- *B06B 1/06* (2006.01)
- *G01D 5/12* (2006.01)
- *G01N 29/34* (2006.01)
- *G10K 11/30* (2006.01)
- *G01N 29/22* (2006.01)

(52) U.S. Cl.
CPC ........... *G01N 29/221* (2013.01); *G01N 29/34* (2013.01); *G10K 11/30* (2013.01); *G01N 2291/101* (2013.01); *G01N 2291/106* (2013.01)

(58) Field of Classification Search
USPC .......... 73/661, 628, 632, 641, 642; 600/462, 600/472
See application file for complete search history.

(56) References Cited

U.S. PATENT DOCUMENTS

| | | | |
|---|---|---|---|
| 5,622,177 | A | 4/1997 | Breimesser et al. |
| 5,644,085 | A * | 7/1997 | Lorraine ............... B06B 1/0629 29/25.35 |
| 5,680,863 | A | 10/1997 | Hossack |
| 5,735,282 | A | 4/1998 | Hossack |
| 6,736,779 | B1 | 5/2004 | Sano et al. |
| 7,637,871 | B2 | 12/2009 | Freiburger et al. |
| 7,821,180 | B2 | 10/2010 | Kunkel, III |
| 7,878,977 | B2 | 2/2011 | Mo et al. |
| 7,892,175 | B2 * | 2/2011 | Wakabayashi ............ A61B 8/12 600/437 |
| 2002/0035328 | A1 | 3/2002 | Roundhill et al. |
| 2002/0065464 | A1 | 5/2002 | Murphy et al. |
| 2002/0120193 | A1 | 8/2002 | Chiang et al. |
| 2002/0157472 | A1 | 10/2002 | Stephens et al. |
| 2004/0000841 | A1 | 1/2004 | Phelps et al. |
| 2004/0054289 | A1 | 3/2004 | Eberle et al. |
| 2005/0108667 | A1 | 5/2005 | Iadanza et al. |
| 2007/0272020 | A1 * | 11/2007 | Schneider ............... G01N 29/06 73/628 |
| 2008/0134793 | A1 | 6/2008 | Woychik et al. |
| 2008/0195003 | A1 * | 8/2008 | Sliwa ....................... A61N 7/02 601/3 |
| 2009/0182229 | A1 | 7/2009 | Wodnicki |
| 2009/0243436 | A1 * | 10/2009 | Rubinsztajn ........... G10K 11/30 310/335 |
| 2010/0280388 | A1 | 11/2010 | Huang et al. |
| 2010/0324423 | A1 | 12/2010 | El-Aklouk et al. |
| 2011/0172537 | A1 | 7/2011 | Hongou et al. |
| 2012/0206014 | A1 | 8/2012 | Bibl et al. |
| 2012/0235539 | A1 | 9/2012 | Bibl et al. |
| 2013/0310693 | A1 | 11/2013 | Tsuruno |
| 2014/0013850 | A1 * | 1/2014 | Kim .................... G01N 29/2406 73/640 |
| 2014/0117812 | A1 | 5/2014 | Hajati |
| 2015/0272545 | A1 * | 10/2015 | Atsuchi .................... A61B 8/42 600/459 |

OTHER PUBLICATIONS

Hajati, U.S. Appl. No. 14/292,438, entitled: "Piezoelectric Transducer Device With Flexible Substrate", filed May 30, 2014, pp. 60.
Hajati, et al., U.S. Appl. No. 14/292,413, entitled: "Piezoelectric Transducer Device for Configuring a Sequence of Operational Modes", filed May 30, 2014, pp. 60.
Non-Final Office Action from U.S. Appl. No. 14/292,438 mailed Sep. 21, 2016, 14 pgs.
Non-Final Office Action from U.S. Appl. No. 14/292,413 mailed Aug. 30, 2016, 14 pgs.
International Preliminary Report on Patentability for PCT Patent Application No. PCT/US15/32659 mailed Dec. 15, 2016, 6 pgs.
International Preliminary Report on Patentability for PCT Patent Application No. PCT/US15/32661 mailed Dec. 15, 2016, 8 pgs.
International Preliminary Report on Patentability for PCT Patent Application No. PCT/US15/32662 mailed Dec. 15, 2016, 6 pgs.
Final Office Action for U.S. Appl. No. 14/292,413 mailed Dec. 27, 2016, 12 pgs.
International Search Report and Written Opinion PCT Application No. PCT/US2015/032659 mailed Aug. 26, 2015, 8 pages.
International Search Report and Written Opinion PCT Application No. PCT/US2015/032661 mailed Sep. 15, 2015, 10 pages.
International Search Report and Written Opinion PCT Application No. PCT/US2015/032662, mailed Aug. 25, 2015, 8 pages.
Non-Final Office Action from U.S. Appl. No. 14/292,413 mailed Apr. 11, 2017, 15 pgs.
Final Office Action from U.S. Appl. No. 14/292,438 mailed May 4, 2017, 7 pgs.

* cited by examiner

Sequence 500

Sequence 510

Sequence 520

Sequence 530

PIEZOELECTRIC TRANSDUCER DEVICE WITH LENS STRUCTURES

RELATED APPLICATION

This application claims priority to U.S. application Ser. No. 14/292,413 filed on May 30, 2014, entitled "PIEZOELECTRIC TRANSDUCER DEVICE FOR CONFIGURING A SEQUENCE OF OPERATIONAL MODES", and U.S. application Ser. No. 14/292,438, filed on May 30, 2014, entitled "PIEZOELECTRIC TRANSDUCER DEVICE WITH FLEXIBLE SUBSTRATE".

BACKGROUND

1. Technical Field

This specification relates generally to piezoelectric transducers.

2. Background Art

A piezoelectric transducer includes a piezoelectric element capable of converting electrical energy into mechanical energy (e.g., sound or ultrasound energy), and vice versa. Thus, a piezoelectric transducer can serve both as a transmitter of mechanical energy and a sensor of impinging mechanical energy.

An ultrasonic piezoelectric transducer device can include a piezoelectric vibrating element that vibrates at a high frequency in response to a time-varying driving voltage, and generates a high frequency pressure wave in a propagation medium (e.g., air, water, or tissue) in contact with an exposed outer surface of the vibrating element. This high frequency pressure wave can propagate into other media. The same vibrating element can also receive reflected pressure waves from the propagation media, and convert the received pressure waves into an electrical signal. The electrical signal can be processed in conjunction with the driving voltage signal to obtain information on variations of density or elastic modulus in the propagation media.

An ultrasonic piezoelectric transducer device can include an array of piezoelectric vibrating elements, each vibrating element can be individually controlled with a respective driving voltage and/or pulse width and time delay, such that a pressure wave having a desired direction, shape, and focus can be created in the propagation medium by the array of vibrating elements collectively, and information on the variations of density or elastic modulus in the propagation media can be more accurately and precisely ascertained based on the reflected and/or refracted pressure waves captured by the array of piezoelectric vibrating elements.

BRIEF DESCRIPTION OF THE DRAWINGS

The various embodiments of the present invention are illustrated by way of example, and not by way of limitation, in the figures of the accompanying drawings and in which.

DETAILED DESCRIPTION

Figure 1A:
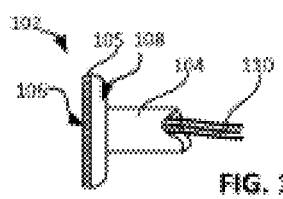
FIGS. 1A-1H illustrate example configurations of piezoelectric transducer devices that include array(s) of vibrating elements.

A piezoelectric ultrasonic transducer device is capable of generating high frequency pressure waves in a propagation medium (e.g., air, water, tissue, bone, metal, etc.) using a piezoelectric transducer array vibrating in response to a high frequency time-varying driving voltage. An exposed outer surface of the vibrating transducer array can be placed close to or in contact with the propagation medium to couple the energy carried by the vibrations of the exposed outer surface to the energy carried by the pressure waves propagating along one or more directions in the propagation medium. An ultrasonic transducer device typically generates sound waves with frequencies above the human audial range. However, in some implementations, piezoelectric transducer devices made according to the descriptions in this specification can be used to generate sound waves with frequencies within or below the human audial range as well.

When the pressure waves encounter variations in density or elastic modulus (or both) either within the propagation medium or at a boundary between media, the pressure waves are reflected. Some of the reflected pressure waves can be captured by the exposed outer surface of the transducer array and converted to voltage signals that are sensed by the sensing circuits of the ultrasonic transducer device. The sensed voltage signals can be processed in conjunction with the driving voltage signals to obtain information on the variations in density or elastic modulus (or both) within the propagation medium or at the boundary between the media.

When the vibrations of each vibrating element in the vibrating transducer array are individually controlled and timed with respective time delays and frequencies, a wave front having a desired shape, size, direction, and speed can be generated. The size and pitch of the vibrating elements, the layout of the transducer array, the driving frequencies, and the respective time delays and locations of the vibrating elements, can be used in conjunction with the respective strength and timing of the sensed voltage signals on the vibrating elements, to determine the variations in density or elastic modulus (or both) either within the propagation medium, and to deduce the locations, sizes, shapes, and/or speeds of the objects and/or structural variations encountered by the pressure waves in the propagation medium. The deduced information on the locations, size, shapes, and/or speeds of the objects and/or structure variations in the propagation medium can be presented on an external display device, for example, as colored or monochromatic images. Ultrasonic transducer devices can find many applications in which imaging of internal structural variations within a medium or multiple media is of interest, such as in medical diagnostics, product defect detection, minimally-invasive surgery equipment, etc.

Certain embodiments variously provide a device (for brevity, referred to herein as a "tile") which includes a plurality of piezoelectric transducers elements and a base structure (or simply "base") which adjoins and supports the individual piezoelectric transducers elements. The base may include integrated circuitry which is programmed or otherwise configured to variously implement any of a plurality of operational modes of the tile. For example, the base may be pre-programmed with a sequence of operational modes. Instead of relying on comparatively high voltage (HV) analog switches, as in conventional (and less integrated) approaches, certain embodiments allow for better integration by using low voltage (LV)—e.g. 3.3V—analog switches to select transducer elements for operation. For example, certain embodiments provide some measure of separation between comparatively high voltage drive/transmit functionality of a tile and lower sense/receive functionality of the tile. LV analog switches are significantly smaller than a HV analog switch which have similar on-resistance (Ron). In addition, LV analog switches may not require level-shifter and/or gate driver circuitry.

Volumetric—or three-dimensional (3D)—imaging may be performed with one or more configurable (e.g. including reconfigurable) tiles which each include a respective two dimensional (2D) array of piezoelectric transducer elements. For example, a plurality of configurable tiles may be variously disposed on a curved surface of a probe, wherein the plurality of tiles operate to image a wedge, cone or other tapered volume which, for example, is defined as a projection from a portion of the curved surface. During operation of the probe, the plurality of tiles may be variously reconfigured over time—e.g. to increase, decrease, move or otherwise change the volume to be imaged. Alternatively or in addition, reconfiguring of the plurality of tiles may change the imaging to be performed for a volume of a particular size and location.

Certain other embodiments variously provide a device comprising a flexible (e.g. plastic film) substrate and a plurality of tiles coupled to the substrate. Coupling of the flexible substrate to the tiles may be performed, for example, with operations adapted from conventional flexible MEMS techniques. The substrate may have disposed therein or thereon signal lines for exchanging signals to, from or between the plurality of tiles. Accordingly, the substrate may serve as a backplane for an exchange between the device and a remote system for processing and/or communicating image information. Some or all of the tiles may each be pre-programmed to implement any of a respective plurality (e.g. a sequence) of operational modes, although certain embodiments are not limited in this regard. The flexible substrate may allow for the plurality of tiles to be bonded (e.g. adhered) or otherwise coupled to a surface of a probe device which includes a very small radius of curvature.

Still other embodiments variously provide one or more curved lens structures to facilitate the shaping of a wave propagating from a probe device. The probe device may include a portion having a curved surface and a plurality of tiles variously coupled to the curved surface. Some or all such tiles may be coupled to the curved surface via a flexible membrane, although certain embodiments are not limited in this regard. In one embodiment, a plurality of distinct lenses are each coupled to a respective tile. Alternatively, a single lensing body comprising multiple lens regions may be coupled across multiple tiles.

FIGS. 1A-1G illustrate example configurations of piezoelectric transducer devices that include array(s) of curved vibrating elements. In some implementations, a transducer device includes a transducer array. The elements in the transducer array may be positioned on a substantially flat plane. As shown in FIG. 1A, the transducer device 102 includes a handle portion 104. The transducer array 106 can be attached to the handle 104 at one distal end 108 of the handle 104, where the shape of the handle 104 is modified (e.g., widened, flattened, etc.) to accommodate the shape and size of the transducer array 106. In this example, the vibrating outer surface of the transducer array 106 faces a forward-direction along the long axis of the handle 104, i.e., the outer surface 105 of the substrate on which the array 106 is fabricated is perpendicular to the long axis of the handle 104. In other implementations, the exposed outer surface of the transducer array 106 can face to the side along a direction perpendicular (or at an acute angle) to the long axis of the handle 104. An operator of the transducer device 102 can manipulate the handle 104 to change the direction and location of the vibrating outer surface of the linear transducer array 106 as desired (e.g., facing the area(s) to be imaged).

The piezoelectric transducer device 102 can optionally include an integrated application specific integrated circuit (or ASIC, not shown) below the linear array of vibrating elements 106 and inside the handle portion 104 (e.g., inside the widened and flattened first distal end 108). Wires 110 connecting to the external input connections of the ASIC can exit from the back end of the handle 104 and be connected to external equipment (e.g., a control device and/or a display device).

In some implementations, transducer devices can include two dimensional transducer arrays. Each two-dimensional transducer array can include multiple curved vibrating elements distributed in a two-dimensional array. The area covered by the two-dimensional array can be of various shapes, e.g., rectangular, square, circular, octagonal, hexagonal, circular, and so on. The vibrating elements in the two-dimensional array can be distributed on a lattice consisting of straight lines (e.g., a square lattice or hexagonal lattice) or of more complex patterns. The vibrating outer surface of the two-dimensional transducer array can be substantially within a plane as well. The two-dimensional transducer array can be attached to a handle (e.g., at one distal end of a straight cylindrical handle) to form the transducer device. The plane of the vibrating outer surface of the transducer array can face forward, e.g., be perpendicular to, the long axis of the handle (e.g., as shown in FIG. 1B), or face to the side, i.e., be parallel (or at an acute angle), to the long axis of the handle (e.g., as shown in FIG. 1C).

An operator of the transducer device can manipulate the handle of the transducer devices to change the facing direction and location of the vibrating outer surface of the two-dimensional transducer array as desired (e.g., facing the area(s) to be imaged).

Figure 1B:
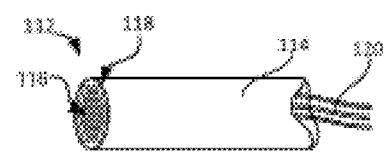

As shown in FIG. 1B, the piezoelectric transducer device 112 includes a forward facing hexagonal transducer array 116 attached to a handle 114 at a first distal end 118. The piezoelectric transducer device 112 can optionally include an integrated ASIC (not shown) below the hexagonal array of vibrating elements and inside the handle portion 114. Wires 120 connecting to the external connections of the ASIC can exit from the back (e.g., a second distal end) of the handle 114 and be connected to external equipment (e.g., a control device and/or a display device). The forward facing transducer device 112 can be used for intravascular ultrasound (IVUS) imaging, which is not feasible with conventional ultrasound imaging.

Figure 1C:
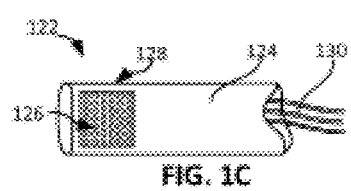

FIG. 1C shows a piezoelectric transducer device 122 that includes a side-facing square transducer array 126 attached to a handle 124 at a first distal end 128. The piezoelectric transducer device 122 can optionally include an integrated ASIC (not shown) on the back of the square array of vibrating elements and inside the handle portion 124. Wires 130 connecting the external connections of the ASIC can exist from the back (e.g., a second distal end) of the handle 124 and be connected to external equipment (e.g., a control device and/or display device).

In some implementations, a transducer device can include a one-dimensional transducer array or a two-dimensional transducer array that is wrapped along a curved line or around a curved surface, such that the vibrating outer surface of the transducer array is a curved line or curved surface.

Figure 1D:
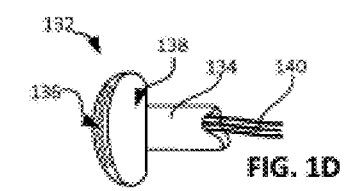

For example, FIG. 1D shows an example transducer device 132 that includes a linear transducer array 136 that runs along a curved line and attached to a handle 134 at a first distal end 138 (e.g., an enlarged, curved, and flattened portion) of the handle 134. The transducer device 132 also includes wires 140 connected to an ASIC (not shown) and exiting a back end of the handle 134.

Figure 1E:
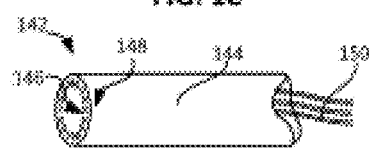

FIG. 1E shows an example transducer device 142 that includes a forward-facing linear transducer array 146 that runs around the circumference of a circle and attached to a handle 144 at a distal end 148 of the handle 144. The transducer device 142 also includes wires 150 connected to an ASIC (not shown) and exiting a back end of the handle 144.

Figure 1F:
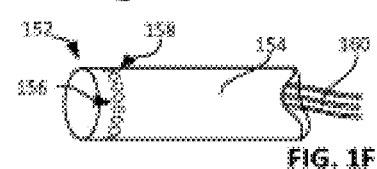

FIG. 1F shows an example transducer device 152 that includes a side-facing linear transducer array 156 that runs around the circumference of a circle and attached to a handle 154 at a distal end 158 of the handle 154. The transducer device 152 also includes wires 160 connected to an ASIC (not shown) and exiting a back end of the handle 154.

Figure 1G:
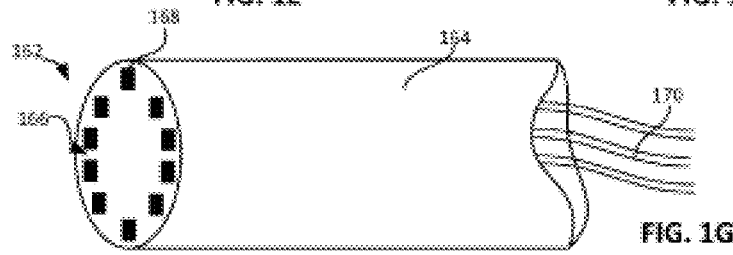

In some implementations, each vibrating element of the linear transducer arrays 136, 146, and 156 shown in FIGS. 1D, 1E, and 1F can be replaced by a small two-dimensional sub-array. For example, each sub-array can be a small square transducer array. As shown in FIG. 1G, a transducer device 162 includes a forward-facing two-dimensional annular array 166 formed of multiple square sub-arrays of vibrating elements (e.g., square sub-arrays 168), where the forward-facing annular array 166 is attached to a first distal end of a handle 164 of the transducer device 162. The transducer device 162 also includes wires 170 connected to an ASIC (not shown) and exiting a back end of the handle 164.

Figure 1H:
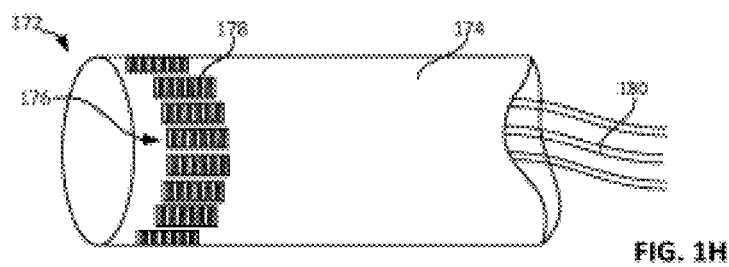

Similarly, as shown in FIG. 1H, a transducer device 172 includes a side-facing array 176 formed of multiple square sub-arrays of vibrating elements (e.g., square sub-arrays 178), where the side-facing array 176 is attached to a first distal end of a handle 174 of the transducer device 172. The transducer device 172 also includes wires 180 connected to an ASIC (not shown) and exiting a back end of the handle 174.

The configurations of the transducer devices shown in FIGS. 1A-1H are merely illustrative. Different combinations of the facing direction (e.g., forward-facing, side-facing, or other facing angles) and overall shape (e.g., flat or curved, linear, polygonal, or annular) of the vibrating outer surface of entire transducer array, the positions of the transducer array on the handle, and the layout of the vibrating elements on the transducer array are possible in various implementations of the transducer devices.

In addition, depending on the applications (e.g., the desired operating frequencies, imaged area, imaging resolutions, etc.), the total number of vibrating elements in the transducer array, the size of the transducer array, and the size, pitch and/or distribution of the vibrating elements in the transducer array can also vary. In one example, a linear array includes 128 vibrating elements of 50 micron radii at a 200 micron pitch. In another example, a square array includes 16 vibrating elements of 75 microns at a 200 micron pitch. For example, individual vibrating elements (such as 50 to 150 micron diameter convex or concave domes) may be arranged in tightly-packed small pitch clusters of two to four—e.g. where a larger pitch separates the centers of such clusters. In one illustrative embodiment, an array may comprise 128 vibrating elements, each of which includes a cluster of two to four smaller domes, where a pitch between the elements is (for example) 200 microns. Other example configurations may be variously provided according to different embodiments.

Figure 2A:
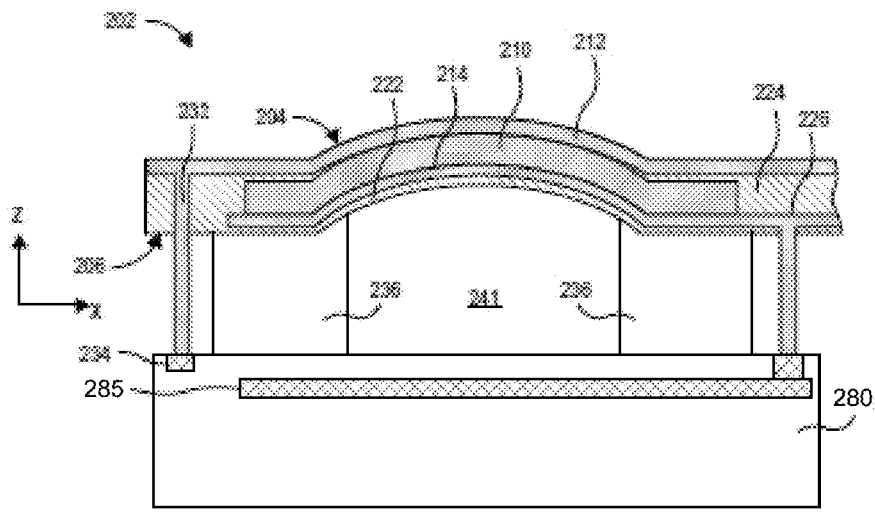
FIG. 2A-2C illustrate vertical cross-sections of example piezoelectric transducer devices including vibrating elements.
Figure 2B:
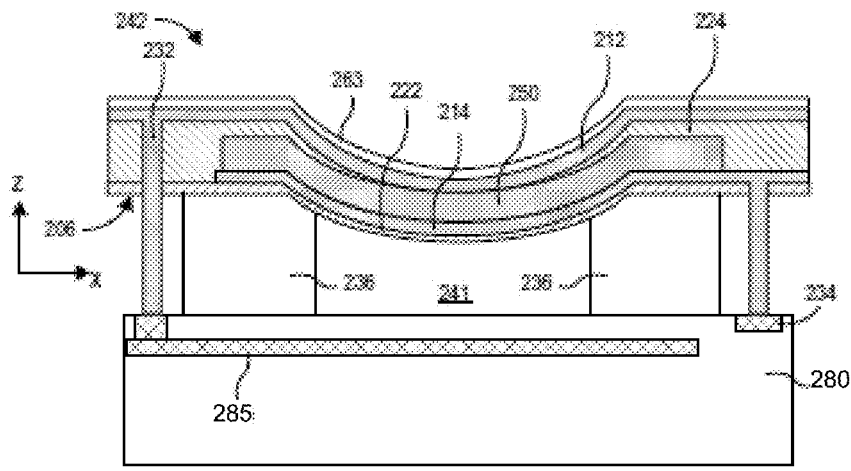
Figure 2C:
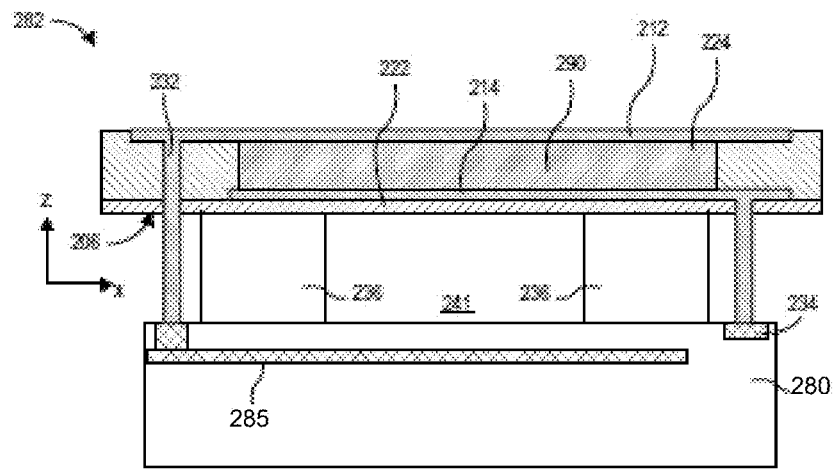

In the context of FIGS. 2A-2C, exemplary micromachined (i.e., microelectromechanical or MEMS) aspects of individual transducer elements are now briefly described. It is to be appreciated that the structures depicted in FIGS. 2A-2C are included primarily as context for particular aspects of particular embodiments and to further illustrate the broad applicability of various embodiments with respect to piezoelectric transducer device structures.

In FIG. 2A, a convex transducer element 202 includes a top surface 204 that during operation forms a portion of a vibrating outer surface of a piezoelectric MEMS ultrasound transducer (pMUT) array. The transducer element 202 also includes a bottom surface 206 that is attached to a top surface of the substrate 280. The transducer element 202 includes a convex or dome-shaped piezoelectric membrane 210 disposed between a reference electrode 212 and a drive/sense electrode 214. In one embodiment, the piezoelectric membrane 210 can be formed by depositing (e.g., sputtering) piezoelectric material particles in a uniform layer on a profile-transferring substrate (e.g., patterned silicon) that has a dome formed on a planar top surface, for example. An exemplary piezoelectric material is Lead Zirconate Titanate (PZT), although any known in the art to be amenable to conventional micromachine processing may also be utilized, such as, but not limited to polyvinylidene difluoride (PVDF) polymer particles, BaTiO3, single crystal PMN-PT, and aluminum nitride (AlN). The drive/sense electrode and reference electrode 214, 212 can each be a thin film layer of conductive material deposited (e.g., by PVD, ALD, CVD, etc.) on the profile-profile transferring substrate. The conductive materials for the drive electrode layer can be any known in the art for such function, such as, but not limited to, one or more of Au, Pt, Ni, Ir, etc.), alloys thereof (e.g., AdSn, IrTiW, AdTiW, AuNi, etc.), oxides thereof (e.g., IrO2, NiO2, PtO2, etc.), or composite stacks of two or more such materials.

Further as shown in FIG. 2A, in some implementations, the transducer element 202 can optionally include a thin film layer 222, such as silicon dioxide that can serve as a support and/or etch stop during fabrication. A dielectric membrane 224 may further serve to insulate the drive/sense electrode 214 from the reference electrode 212. Vertically-oriented electrical interconnect 226 connects the drive/sense electrode 214 to drive/sense circuits via the drive/sense electrode rail 285. A similar interconnect 232 connects the reference electrode 212 to a reference rail 234. An annular support 236, having a hole 241 with an axis of symmetry defining a center of the transducer element 202, mechanically couples the piezoelectric membrane 210 to the substrate 280. The support 236 may be of any conventional material, such as, but not limited to, silicon dioxide, polycrystalline silicon, polycrystalline germanium, SiGe, and the like. Exemplary thicknesses of support 236 range from 10-50 μm and exemplary thickness of the membrane 224 range from 2-20 μm.

FIG. 2B shows another example configuration for a transducer element 242 in which structures functionally similar to those in transducer element 202 are identified with like reference numbers. The transducer element 242 illustrates a concave piezoelectric membrane 250 that is concave in a resting state. Here, the drive/sense electrode 214 is disposed below the bottom surface of the concave piezoelectric membrane 250, while the reference electrode 212 is disposed above the top surface. A top protective passivation layer 263 is also shown.

FIG. 2C shows another example configuration for a transducer element 282 in which structures functionally similar to those in transducer element 202 are identified with like reference numbers. The transducer element 282 illustrates a planar piezoelectric membrane 290 that is planar in a resting state. Here, the drive/sense electrode 214 is disposed below the bottom surface of the planar piezoelectric membrane 290, while the reference electrode 212 is disposed above the top surface. An opposite electrode configuration from that depicted in each of FIGS. 2A-2C is also possible.

Figure 3:
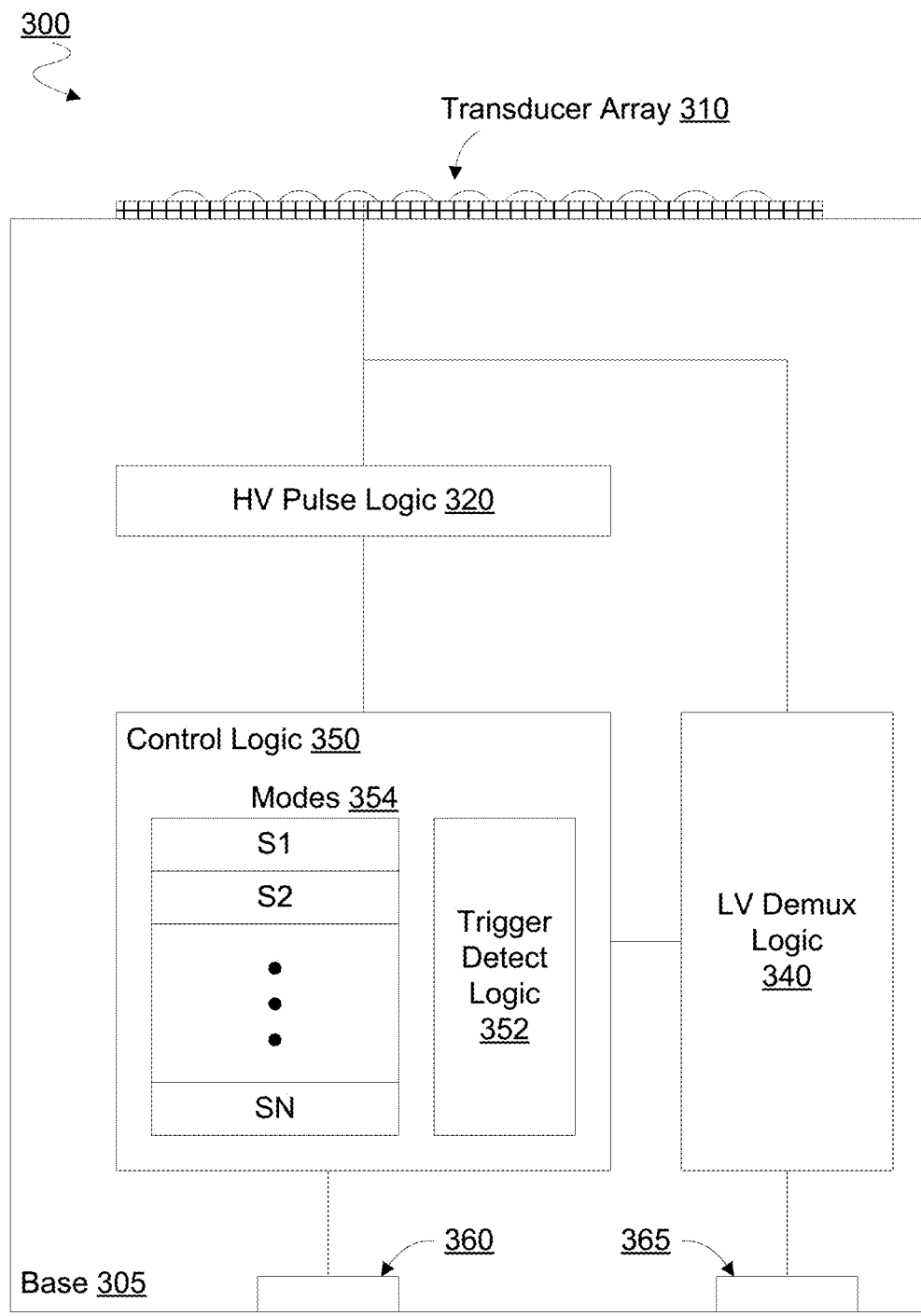
FIG. 3 is a functional block diagram illustrating elements of a piezoelectric transducer device according to an embodiment.

FIG. 3 illustrates elements of a tile 300 according to an embodiment for providing signals representing ultrasound (or other) imaging information. Tile 300 is one example of a device which includes an array of piezoelectric transducer elements and integrated circuitry—e.g., including pulse logic, demultiplexer logic and/or digital control logic—for operation of the array. For brevity, an integrated combination of a piezoelectric array and such a supporting base is referred to herein as a "tile." Such integrated circuitry may be part of a base which adjoins and physically supports the array. For example, tile 300 may be a packaged device. Certain embodiments provide for demultiplex logic of the base to be part of a voltage domain which is characterized by a relatively low operational voltage level (or voltage range)—e.g. as compared to a corresponding operational voltage level (range) of another voltage domain of the base.

By way of illustration and not limitation, tile 300 may include a base 305 and a transducer array 310 supported by one side of base 305. For example, base 305 may include a substrate such as any of those variously supporting transducer structures in FIGS. 2A-2C. Base 305 may comprise integrated circuitry—e.g. including a single integrated circuit (IC) die or an IC die stack—which is programmed to implement any of a plurality of operational modes, each mode for respective operation of transducer array 305 to generate image information. In one embodiment, base 305 includes control logic 350—e.g. including a microcontroller or the like—to receive signals provided to tile 300 from an external system (not shown)—e.g. including control signals received via a control interface 360. The control signals may program control logic 350 to be able to implement any of a plurality of operational modes of tile 300. The illustrative modes 354 programed in control logic 350 represent one example of such a plurality of operational modes of tile 300. Alternatively, the control signals may be provided to tile 300 via interface 360 after control logic 350 is already programmed with modes 354.

The programming of modes 354 may include providing to (or otherwise defining with) control logic 350 respective state information S1, S2, . . . , SN each to implement at least in part a respective operational mode. Although certain embodiments are not limited in this regard, state information S1, S2, . . . , SN may be variously stored in a memory of control logic 350. Alternatively or in addition, control logic 350 may include circuitry such as that of a field programmable gate array (FPGA) or other programmable gate array (PGA), where such circuitry is programmable to implement a state machine or other logic to variously configure modes 354 represented by state information S1, S2, . . . , SN. However, certain embodiments are not limited with respect to a particular mechanism whereby control logic 350 is to implement any of modes 354.

For a given one of modes 354, state information for configuring the mode may include, for example, address, bitmap or other information specifying a subset of the transducer elements of array 310 which are to correspond to the mode. Subsequent configuring of that mode may result in selection of the subset based on such state information—e.g. for activation of only the subset to communicate image information. The state information may also include one or more values each for a respective parameter (e.g. voltage level, time duration, time delay, frequency or the like) characterizing activation of some or all of the subset of transducer elements. For example, each transducer element of a given subset may be selected for activation which is characterized by the same voltage level, time duration, time delay, frequency, etc. Alternatively or in addition, such state information for the mode may include information specifying a demultiplexing to be performed for transmitting image information from device 300. For example, each transducer element of a given subset may be selected to be switchedly connected to the same signal line of a bus.

A subset of piezoelectric transducer elements for a given mode may include all piezoelectric transducer elements of array 310 which are to be operated according to that given mode. The mode may specify or otherwise determine that the subset of elements are to be variously coupled, according to the mode, each to provide a respective signal to be output from tile 300. The mode may associate elements of the corresponding subset each with a respective signal line (not shown) which is to couple to tile 300—e.g. via an interface 365. For example, the mode may variously associate such elements each with a respective one of multiple pads, pins or other input/output (I/O) contacts (not shown) of interface 365.

By way of illustration and not limitation, a mode may switchedly couple elements of a subset each with a different respective path for outputting signals from tile 300. Alternatively or in addition, such a mode may switchedly couple multiple elements of a subset to the same path for outputting signals from tile 300. To avoid obscuring certain features of various embodiments, modes are variously discussed herein with respect to associating piezoelectric transducer elements each with a different respective line of a signal bus with this a tile is to transmit (and in some embodiments, receive) signals. However, such a mode may additionally or alternatively associate a plurality of piezoelectric transducer elements with the same respective line of such a signal bus.

In an embodiment, control logic 350 includes trigger detect logic 352 to detect that one or more conditions constitute a trigger event for configuring one of modes 354. Such a trigger event may be indicated at least in part by, for example, a control, clock or other signal received by tile 300. Alternatively or in addition, a trigger event may be indicated by an expiration of a period of time or some other condition determined independently by device 300. Prior to detection of the trigger event, control logic 350 may already be programmed with state information S1, S2, ..., SN necessary to implement any of modes 354. For example, detection of the trigger event itself may be independent of control logic 350 receiving any state information explicitly describing a next operational mode which is indicated by that trigger event. Consequently, control logic 350 may respond to the trigger event by identifying the next operational mode to configure, where such identifying is performed independent of any state information received by tile 300 during the previous one (or more) operational modes which, for example, explicitly specifies a subset—e.g. any subset—of transducer elements.

During operation, control logic 350 may, in response to signals sent to tile 300, successively configure tile 300 with some or all of operational modes 354—e.g. where such successive configuring is according to a sequence which is predetermined at control logic 350. When a particular mode is configured, operation of transducer array 310 by circuit logic of base 305 may be according to the configured mode. For example, base 300 may include high voltage (HV) pulse logic 320, responsive to control logic 350, to selectively drive (or "activate") at various times different respective subsets of the piezoelectric transducer elements of array 310. Such subsets may each correspond to a different respective one of modes 354.

By way of illustration and not limitation, control logic 350 may include or couple to switch logic (not shown) comprising multiple switches each for a different respective piezoelectric transducer element of array 310. In response to detecting a given trigger event, control logic 350 may select a subset of piezoelectric transducer elements for a next operational mode. Based on such selection, HV pulse logic 320 may activate only those selected transducer elements of array 310 which correspond to the operational mode. In one embodiment, control logic 350 (or switch logic coupled thereto) may further indicate to HV pulse logic 320 one or more parameters (e.g. voltage level, time duration, time delay, frequency or the like) which are to characterize some or all such activation of the selected transducer elements.

Activation of the selected subset of array 310 may result in each of the activated transducer elements outputting a sense signal representing respective image information. Based on an operational mode configured by control logic 350, circuit logic of base 305 may operate to selectively send such image information from tile 300—e.g. for processing by a remote system (not shown). By way of illustration and not limitation, base 305 may further comprise low voltage (LV) demultiplexer (demux) logic 340 variously coupled to each of a plurality of piezoelectric transducer elements of array 310. Demux logic 340 may be further coupled via multiple output signal lines to an interface 365 for sending image data from tile 300. However, a total number of piezoelectric transducer elements of array 310 which are coupled to demux logic 340 may be greater than a total number of the output signal lines coupling demux logic 340 to interface 365. Accordingly, demux logic 340 may variously perform demultiplexing for only a selected subset of the piezoelectric transducer elements each to output image information via a respective signal line to interface 365. Such demultiplexing may be variously configured (e.g. reconfigured) over time by control logic 350 according to a currently configured one of modes 354. For example, during a given operational mode, demux logic 340 may be configured to select for signal communication only those signal lines which the selected transducer elements corresponding to that operational mode. Although distinguished from one another in the example of tile 300, interfaces 360, 365 may be part of the same interface.

The integrated circuitry of base 305 may include multiple voltage domains, where a voltage level (or voltage range) for operation of one such domain is greater than a corresponding voltage level (range) for another such domain. For example, a first voltage domain of base 305 may include demux logic 340, where a second voltage domain of base 305 includes HV pulse logic 320. In such an embodiment, a supply voltage, digital logic level (range) or other such operational characteristic of the first domain may be less than a corresponding operational characteristic of the second voltage domain. As discussed herein, certain embodiments further comprise circuitry (not shown in tile 300) to protect the first voltage domain from a comparatively high voltage level of the second voltage domain. The use of relatively low-voltage demux logic 340 in some embodiments allows base 305 to include efficient mechanisms for communicating image information for different operational modes.

Figure 4:
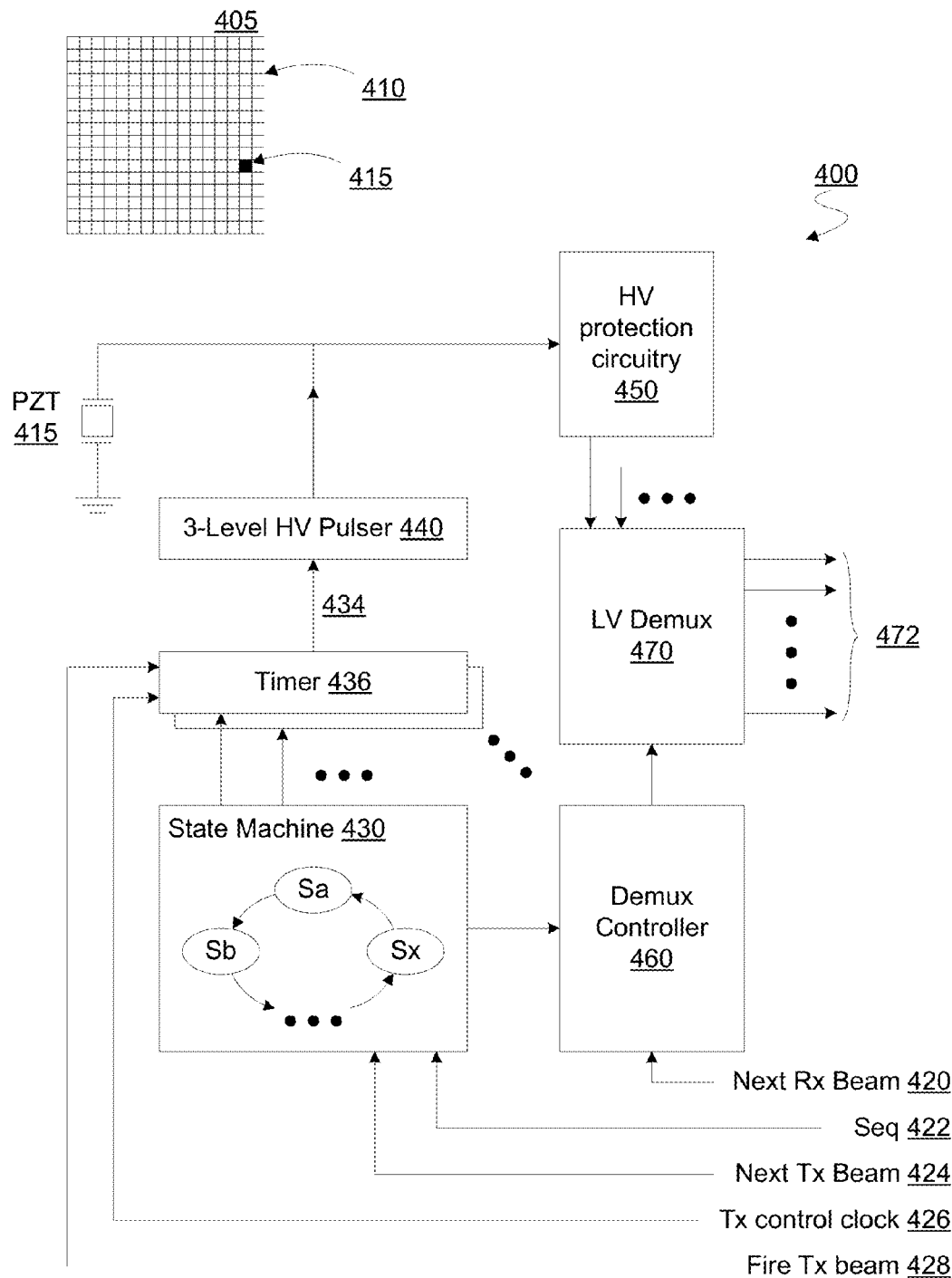
FIG. 4 is a functional block diagram illustrating elements of a piezoelectric transducer device according to an embodiment.

FIG. 4 illustrates elements of a tile 400 according to an embodiment for generating a pressure wave in a medium. Tile 400 illustrates one example of various signals which may be exchanged according to one embodiment for generation and communication of image information. Tile 400 may include some of all of the features of tile 300, although certain embodiments are not limited in this regard.

In an embodiment, tile 400 includes an array 410 of piezoelectric transducer elements which, for example, provides functionality of transducer array 310. Certain features of tile 400 are discussed herein with respect to operation of an illustrative piezoelectric transducer element PZT 415 of array 410—e.g. as shown in view 405. However, such discussion may be extended to additionally or alternatively apply to operation of some or all other transducer elements of array 410.

Array 410 may be adjacent to and supported by a base which, for example, provides some or all of the functionality of base 305. As shown in FIG. 4, such a base may include integrated circuitry to operate array 410 according to various operational modes of tile 400. For example, such integrated circuitry may include control logic which is programmed to implement a state machine 430 for variously transitioning between different operational modes of tile 400. By way of illustration and not limitation, state machine 430 may be configured to successively configure some or all of a sequence of modes Sa, Sb, ..., Sx. The sequence of modes Sa, Sb, ..., Sx may be a repeating sequence, although certain embodiments are not limited in this regard.

In an illustrative embodiment, tile 400 is operable to receive signals—as represented by the illustrative Seq 422—which program state machine 430 for the sequence of operational modes Sa, Sb, ..., Sx. Such programming may be performed before tile 400 receives other signaling for state machine 430 to begin such a sequence. For example, the programming may be performed before tile 400 is to be adapted as a component of some probe device (not shown), and even before manufacturing of tile 400 is complete. In some embodiments, state machine 430 is further programmable and/or reprogrammable to implement one or more additional or alternative mode sequences.

In operation, the control logic of tile 400 may successively configure operational modes Sa, Sb, ..., Sx in response to trigger events which, for example, are indicated by signaling received by tile 400 from a remote system (not shown). Such signaling may include, for example, a next transmit (Tx) beam signal 424 which specifies that state machine 430 is to transition tile 400, according to the sequence, from any currently configured mode for ultrasound beam transmission to another mode for a next ultrasound beam transmission.

The next mode to be configured may, for example, correspond to a particular subset of the transducer elements of array 410 which are to participate in the next ultrasound beam transmission. Configuration of the next operational mode may include state machine 430 generating signaling to directly or indirectly select that particular subset. For example, tile 400 may include multiple circuits each corresponding to a different respective piezoelectric transducer element of array 405. With respect to drive/sense operation of a plurality of piezoelectric transducer elements of array 405, each such circuit may be dedicated to performing drive/sense operation of only one piezoelectric transducer element. By way of illustration and not limitation, circuitry of tile 400 which is dedicated to drive/sense operation of PZT 415 may include timer 436, 3-level HV pulser 440 and HV protection circuitry 450. Similar circuitry of tile 400 (not shown) may be variously dedicated to additional or alternative piezoelectric transducer elements of array 405, according to different embodiments.

In an embodiment, tile 400 includes a plurality of timer circuits each for a different respective one of the transducer elements of array 410. Such timer circuits may include a timer 436 corresponding to PZT 415. Where PZT 415 is to participate in the next beam transmission, state machine 430 may signal timer 436 to indicate selection of PZT 415. State machine 430 may variously signal other such timer circuits to similarly indicate selection of other associated transducer elements of the subset.

In response to state machine 430, timer 434 may send an output 434 to pulse circuitry of tile 400. Although certain embodiments are not limited in this regard, a timing of output 434 may be regulated by one of more signals received by tile 400 by the remote system. By way of illustration and not limitation, timer 436 may receive one or both of a transmit control clock 426 and a fire Tx beam 428 control signal. When set to a particular logic level, the received fire Tx beam 428 may enable timer 436 to output 434—e.g. at a next successive transition (rise or fall) of Tx control clock 426. However, any of a variety of additional or alternative mechanisms may be adapted to control a timing of output 434.

In an embodiment, output 434 is provided to pulse logic of tile 400, such as the illustrative three-level high voltage pulser 440. Pulser 440 may reside in a voltage domain of tile 400 which is characterized by relatively high voltage operation, as compared to one or more other voltage domains of tile 400. Pulser 440 may provide for any of multiple different voltage levels (in this example, three levels) of voltage for driving PZT 415 to generate a pressure wave. A particular one of the different voltage levels may be specified or otherwise indicated by output 434 and/or by other associated signaling from the control logic of tile 400.

In response output 434, pulser 440 may operate PZT 415 for performance of a drive/sense cycle, including PZT 415 generating a pressure wave and, in response to a corresponding return wave, generating a sense signal which represents image information. Such a sense signal may be prepared for subsequent processing in a comparatively low voltage domain of tile 400. For example, the base may further comprise a comparatively low voltage demultiplexer 470 and circuitry—represented by the illustrative HV protection circuitry 450—which is to provide at least partial protection of low voltage demultiplexer 470 from a voltage level of the voltage domain which includes pulser 440.

In an embodiment, transducer elements of array 410 are each coupled via a different respective voltage protection circuit to low voltage demultiplexer 470. For example, PZT 415 may be coupled to provide an output signal to LV demultiplexer 470 via HV protection circuitry 450. Accordingly, at a given time, a selected subset of the transducer elements comprising array 410 may provide sense signals via respective HV protection circuitry to LV demultiplexer 470. HV protection circuitry 450 may include a simple HV switch, a back-to-back diode or any of various other circuitry—e.g. including voltage dividers, operational amplifiers, digital-to-analog converter (DAC) and/or the like—to output comparatively low voltage versions of such sense signals from array 410.

The number of available outputs from HV protection circuitry 450—e.g. one for each transducer element of array 410—may be greater than a total number of signal lines 472 for transmitting from tile 400 the image information for a selected subset. Accordingly, low voltage demultiplexer 470 may perform demultiplexing to select for output via signal lines 472 only those signal lines from HV protection circuitry 450 which correspond to transducer elements of the selected subset. In an embodiment, such demultiplexing may be controlled according to a currently configured one of operational modes Sa, Sb, . . . , Sx. For example, the integrated circuitry of tile 400 may further comprise a demux controller 460 to identify—e.g. based on information from state machine 430—a set of inputs from HV protection circuitry 450 which correspond to a subset of transducer elements selected based on an operational mode. Although certain embodiments are not limited in this regard, demux controller 460 may retrieve such information from state machine 430 in response to a control signal next Rx beam 420 received by tile 400. In some embodiments, next Rx beam 420 and next Tx beam 424 are the same control signal.

Figure 5:
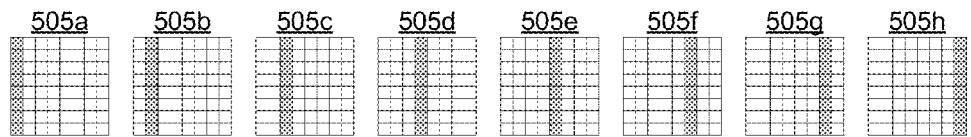
FIG. 5 illustrates various operational modes of each a piezoelectric transducer device according to a respective embodiment.
Figure 5:
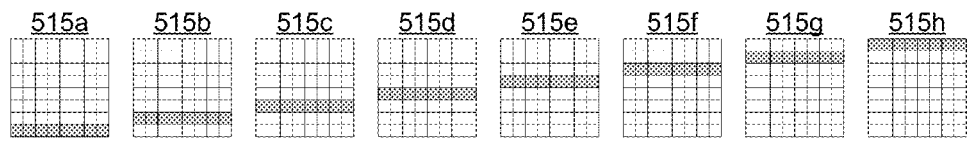
Figure 5:
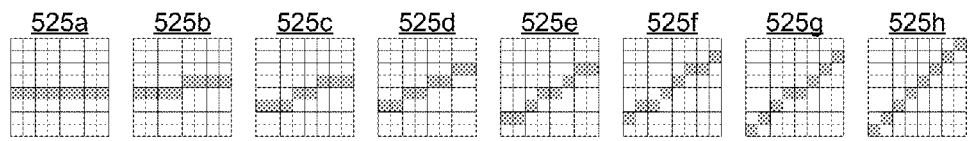
Figure 5:
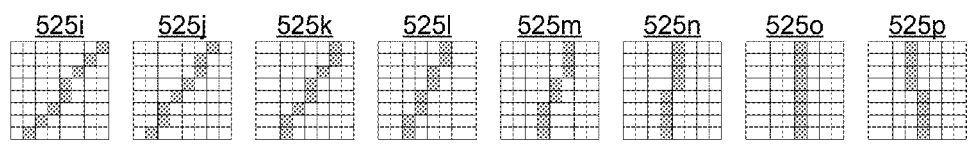
Figure 5:
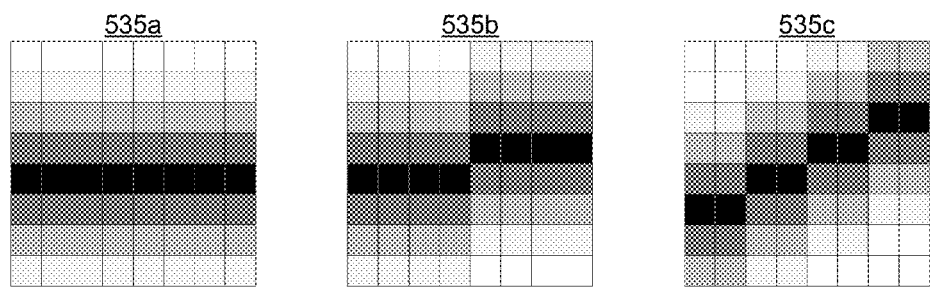

FIG. 5 illustrates elements of various sequences of operational modes, each according to a respective embodiment, for operation of a transducer array. More particularly, FIG. 5 shows, for each of various operational modes, a corresponding selected subset of an array of transducer elements. Certain aspects of various embodiments are discussed herein with respect to an illustrative 8×8 array of transducer elements. However, such discussion may be extended to apply to a pixel array having any of a variety of additional or alternative sizes and/or geometries.

Implementation of a sequence 500 may include successively configuring operational modes 505a-505h—e.g. according to some or all of the techniques discussed herein with respect to tiles 300, 400. As illustrated in sequence 500, operational modes 505a-505h may each correspond to a different respective column of an 8×8 array of transducer elements, where configuration of one of operational modes 505a-505h includes or otherwise results in a selection of the corresponding column of transducer elements. Due to the particular order of sequence 500, successive selection of the columns corresponding to such modes 505a-505h may simulate, for example, translational movement of smaller array—e.g. a one-dimensional (1D) array—in a column-wise direction along the 2D 8×8 array.

In another embodiment, control logic of a tile may be programmed to additionally or alternatively implement a sequence 510 of operational modes 515a-515h. Operational modes 515a-515h may each correspond to a different respective row of an 8×8 (or other) array of transducer elements. Due to the particular order of sequence 510, successive configuration of such modes 515a-515h may result in successive selection of the corresponding rows of the transducer elements, where such successive selection simulates, for example, translational movement of smaller array in a row-wise direction.

In still another embodiment, a sequence of operational modes may serve to simulate rotational movement of a transducer array. For example, sequence 520 includes operational modes 525a-525p which correspond to different respective subsets of an 8×8 array. In turn, such subsets may correspond to different respective lines extending across the array—e.g. where each subset includes the respective transducer elements which are closest to the corresponding line. The order of operational modes 525a-525p—and the associated order of such lines—may result in sequence 520 approximating another (e.g. 1D) array being rotated within the area of the 8×8 array shown.

Sequence 530, which includes operational modes 535a, 535b, 535c, illustrates in more detail another embodiment—similar to that of sequence 520—wherein simulated movement (in this example, rotational movement) of a phased array is achieved. In each of modes 535a, 535b, 535c, transducer elements selected according to the mode are variously driven according to different respective levels of a given operational characteristic. Such an operational characteristic may be, for example, one of a voltage level, a frequency, a time delay, a time duration or the like. Different levels for such an operational characteristic are illustrated for sequence 530 with different shades for transducer elements variously selected according to modes 535a, 535b, 535c. For certain imaging modes, such as one for implementing a Fresnel ring, only a subset of the piezoelectric transducer elements may be connected to an analog bus for communication with a remote system. In other imaging modes, all piezoelectric transducer elements of a tile may be variously coupled to such an analog bus. For example, a mode may switchedly couple multiple piezoelectric transducer elements to the same signal line of the analog bus. Coupling of multiple piezoelectric transducer elements to a common signal line of an analog bus may provide for an improved signal-to-noise ratio.

Figure 6:
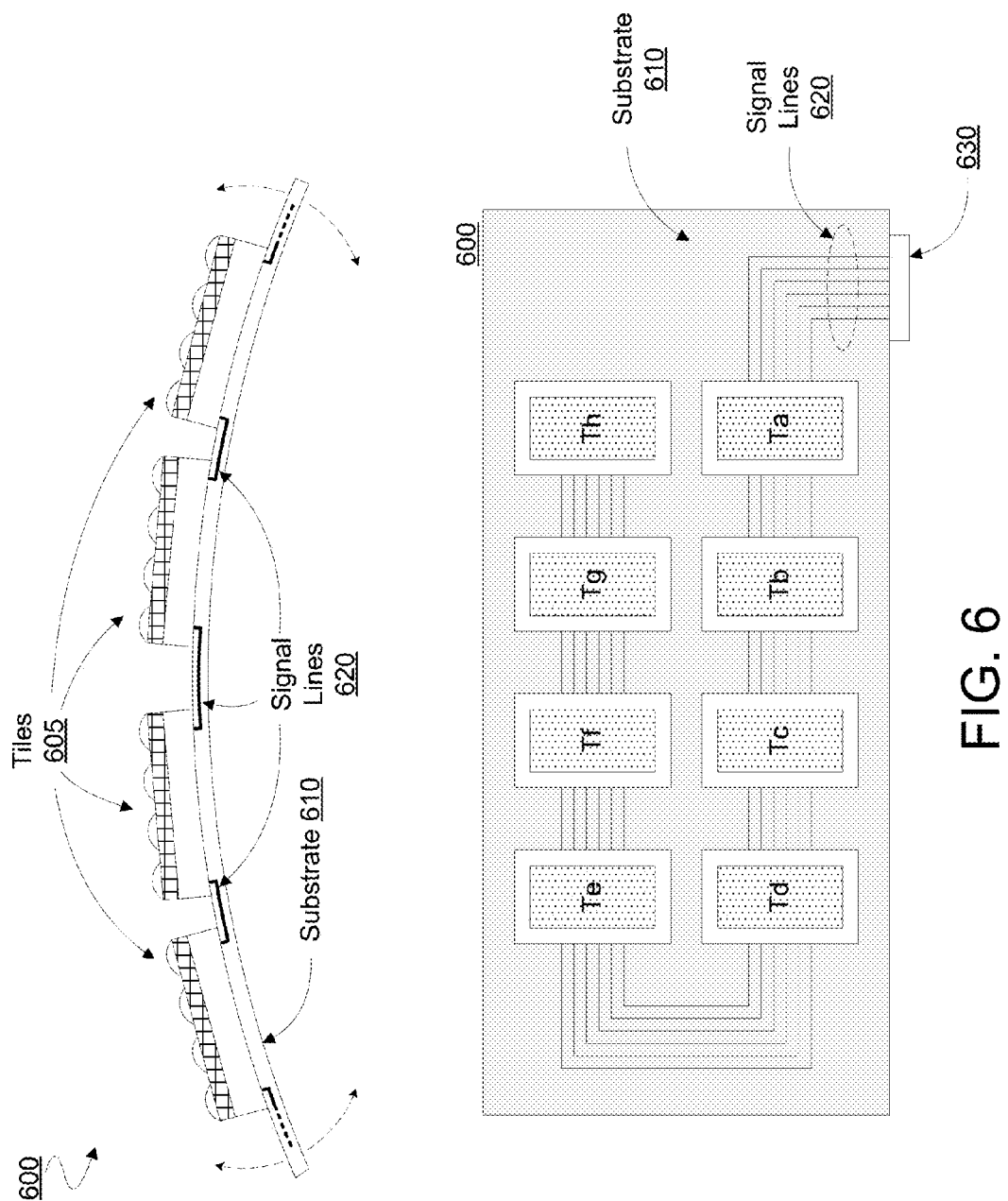
FIG. 6 illustrates elements of a flexible piezoelectric transducer device according to an embodiment.

FIG. 6 illustrates elements of a device 600 for providing ultrasound image information according to an embodiment. Device 600 includes a plurality of tiles 605 which, for example, each variously include some or all of the features of tile 300. Tiles 605 are each coupled to a flexible substrate 610 of device 600, where substrate 610 provides functionality for exchanging signals to, from and/or among tiles 605.

By way of illustration and not limitation, tiles 605 may be arranged in an array, as represented by the illustrative 4×2 array of tiles Ta-Th. Substrate 610 may further comprise an interface 630 and signal lines 620 coupling tiles Ta-Th to interface 630. Signal lines 620 may include one or more buses which, for example, are each to exchange respective data, address and/or control signaling. The particular number of signal lines 620 is merely illustrative, and may vary according to implementation-specific details. Although certain embodiments are not limited in this regard, signal lines in or on substrate 610 may couple tiles Ta-Th in series with one another.

For any given one of tiles Ta-Th, control logic of the tile may programmed for a plurality of operational modes of the tile. Such control logic may receive signals via signal lines 620 and, in response, configure one such operational mode for selective activation of transducer elements of the tile which correspond to the mode. The selective activation of such transducer elements may result in generation of image information which the tile is to transmit via signal lines 620.

In an embodiment, some or all of tiles Ta-Th may be variously pre-programmed each to configure a different respective operational mode in response to the same trigger event indicated by signaling received via interface 630. For example, tile Ta and Tb may have arrays of transducer elements which are of similar geometry and size. Nevertheless, a common trigger event may cause tiles Ta and Tb to select respective transducer elements which are different, for example, in location, geometry, number or the like. Alternatively or in addition, tiles Ta and Tb may select transducer elements for different types of activation—e.g., characterized by different drive voltages, start times, time durations, frequencies or the like.

Figure 7:
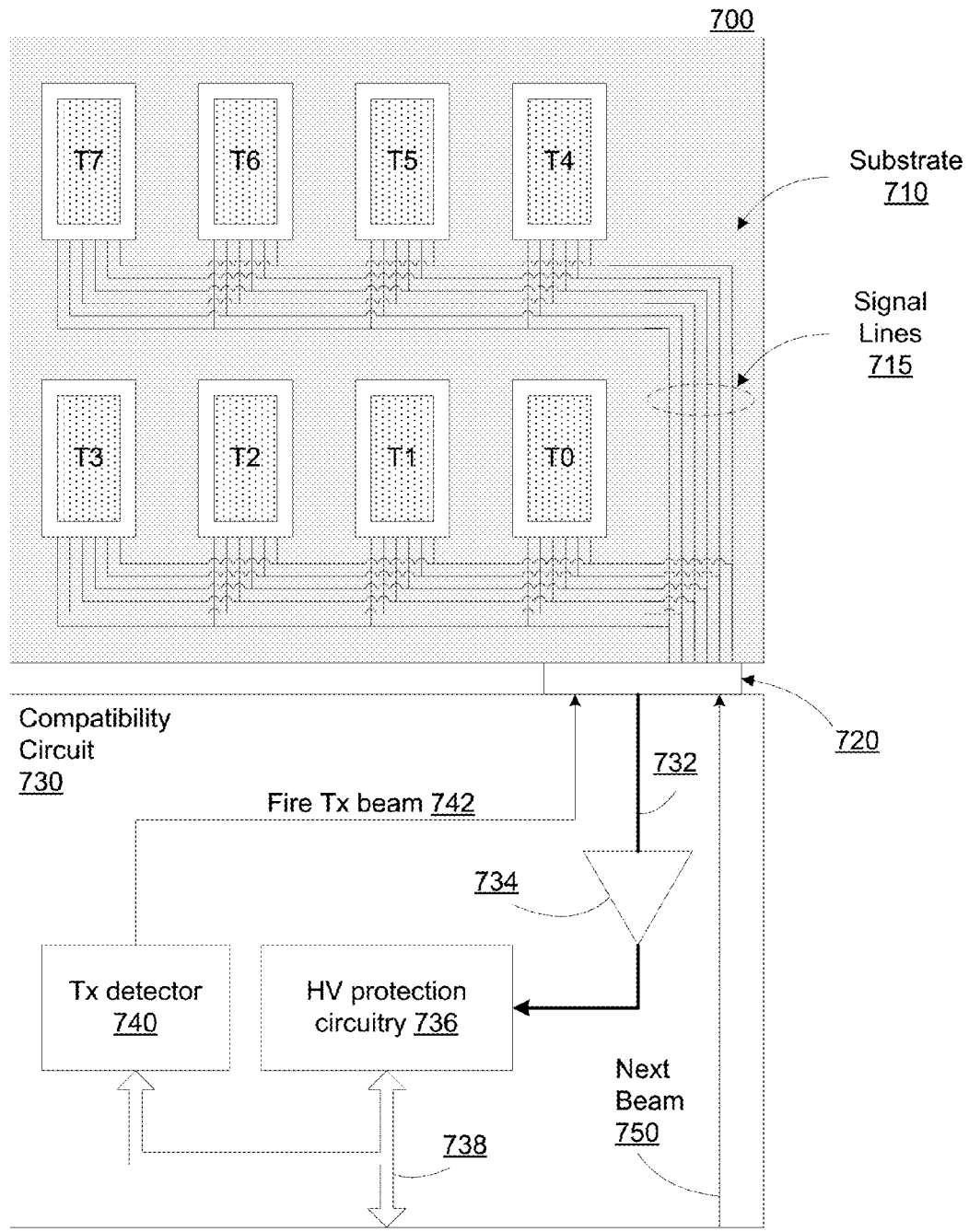
FIG. 7 is a functional block diagram illustrating elements of a piezoelectric transducer assembly according to an embodiment.

FIG. 7 illustrates elements of a system for communicating ultrasound image information according to an embodiment. The system of FIG. 7 includes a device 700 which, for example, may be similar in certain respect to device 600. More particularly, device 700 may include a plurality of tiles T0-T7 which provide functionality corresponding to that of tiles Ta-Th. The plurality of tiles T0-T7 may each be coupled to a flexible substrate 710 having disposed therein or thereon signal lines 715 which variously provide for communication between tiles T0-T7 and an interface 720 by which image information is to be sent from device 700. In the illustrative embodiment of FIG. 7, each of tiles T0-T7 is coupled to interface 720 independent of any other one of tiles T0-T7.

An exchange of signals by a remote system (not shown) with device 700 via interface 720 (or similarly, with device 600 via interface 630) may be facilitated with additional signal processing functionality provided by a programmable compatibility circuit. One example of such a circuit is represented by the illustrative compatibility circuit 730. In one embodiment, compatibility circuit 730 includes functionality such as that of a PGA (e.g. a FPGA) programmability to accommodate operation of a particular type of remote system which is to operate device 700 and process resulting image information received from device 700 and/or amplifier 734.

For example, compatibility circuit 730 may be programmable or otherwise configured to variously pass, reorder, delay, drop, combine, convert or otherwise process any of various control, data and/or other signals received from (or to be sent to) the remote system. By way of illustration and not limitation, compatibility circuit 730 may be programmable to implement a transmit detector 740 to snoop control signals and/or data signals received, for example, at a bus 738 of compatibility circuit 730. Transmit detector 740 may operate to identify certain activity on bus 738 as indicating an opportunity (or need) for transmit/receive cycles to be variously performed by select transducer elements of tiles T0-T7. In response, transmit detector 740 may send to signal lines 715, via interface 720, a signal fire Tx beam 742 which, for example, corresponds functionally to the signal fire Tx beam 428. Alternatively or in addition, compatibility circuit 730 may be configured to pass or otherwise provide a signal next Rx beam 750 which, for example, corresponds to the signal next Tx beam 424. Any of a variety of additional or alternative signal processing may be provided by compatibility circuit 730, according to different embodiments, for operation of device 700.

In response to such control signals, tiles T0-T7 may variously operate to generate signals representing image information. Such signals may be sent via signal lines 715 and interface 720 to compatibility circuit 730 for additional processing in preparation for communicating the image information to the remote system. For example, data signals 732 may be provided to a low noise amplifier 734 for improved transmission to the remote system—e.g. via bus 738. Although certain embodiments are not limited in this regard, compatibility circuit 730 may be programmed or otherwise configured to provide HV protection circuitry 736 which, for example, provides at least partial protection of device 700 from a relatively high voltage of the remote system.

Various embodiments comprise a method for generating image information with, for example, one of tile 300, tile 400, device 600, system 700 or the like. The method may include receiving signals at a device comprising any of various tiles as described herein—e.g. wherein the device is one such tile or includes a plurality of tiles disposed on a flexible substrate. The signals may be received after one or more such tiles are programmed each with a respective plurality of operational modes of the tile—e.g. wherein a tile is programmed with a sequence of operational modes. In response to the received signals, the method may configure one or more operational modes of a tile. For example, a tile of the device may successively configure operational modes according to a preprogrammed sequence. Alternatively or in addition, a plurality of tiles of the device may each configure a respective operational mode.

In an embodiment, the method comprises drive/sense operations each according to a configured operational mode of one or more tiles. By way of illustration and not limitation, the method may comprise, for each of one or more such tiles, activating a subset of a plurality of piezoelectric transducer elements of the tile. The activation may result in one such subset of piezoelectric transducer elements generating image information. In an embodiment, the method further comprises a tile demultiplexing the generated image information for transmission from the tile. Such demultiplexing may be based on configuration of the respective operational mode of the tile. The method may variously perform multiple such drive/sense operations—e.g. including the method performing drive/sense operations each for a successive operational mode of a tile and/or drive/sense operations for different respective tiles of the device.

Figure 8A:
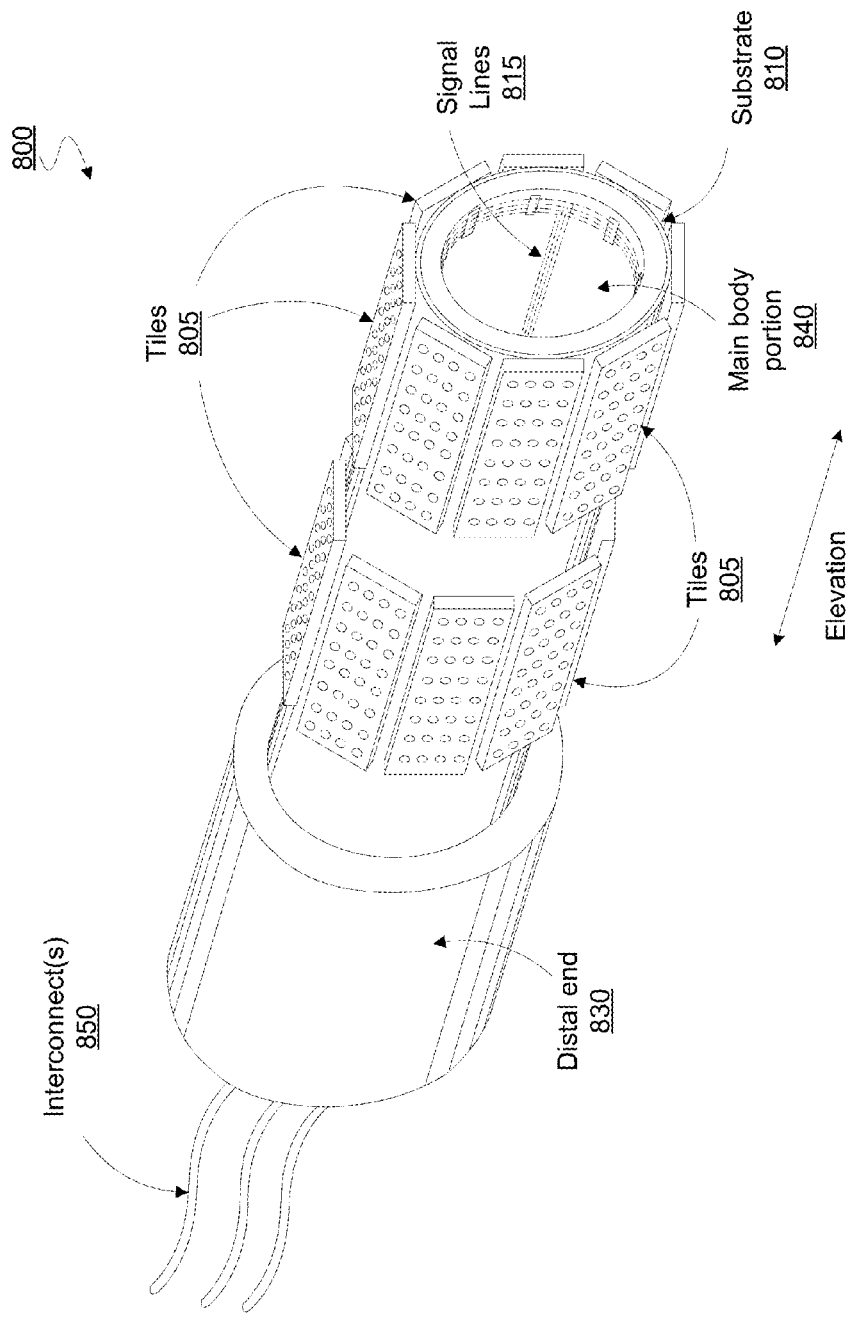
FIGS. 8A, 8B illustrate elements of an ultrasound probe device according to an embodiment.
Figure 8B:
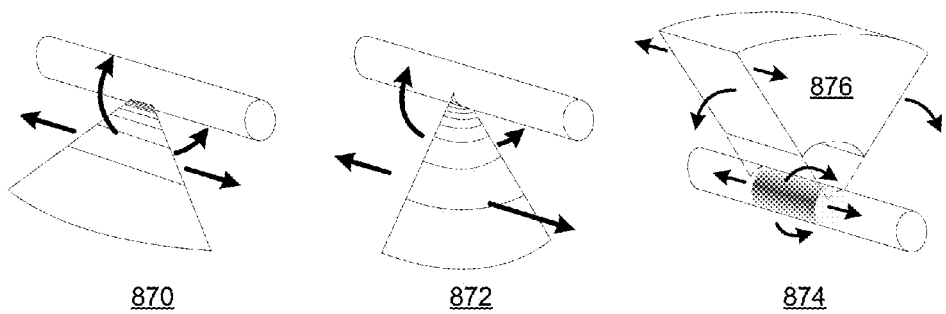
Figure 8B:
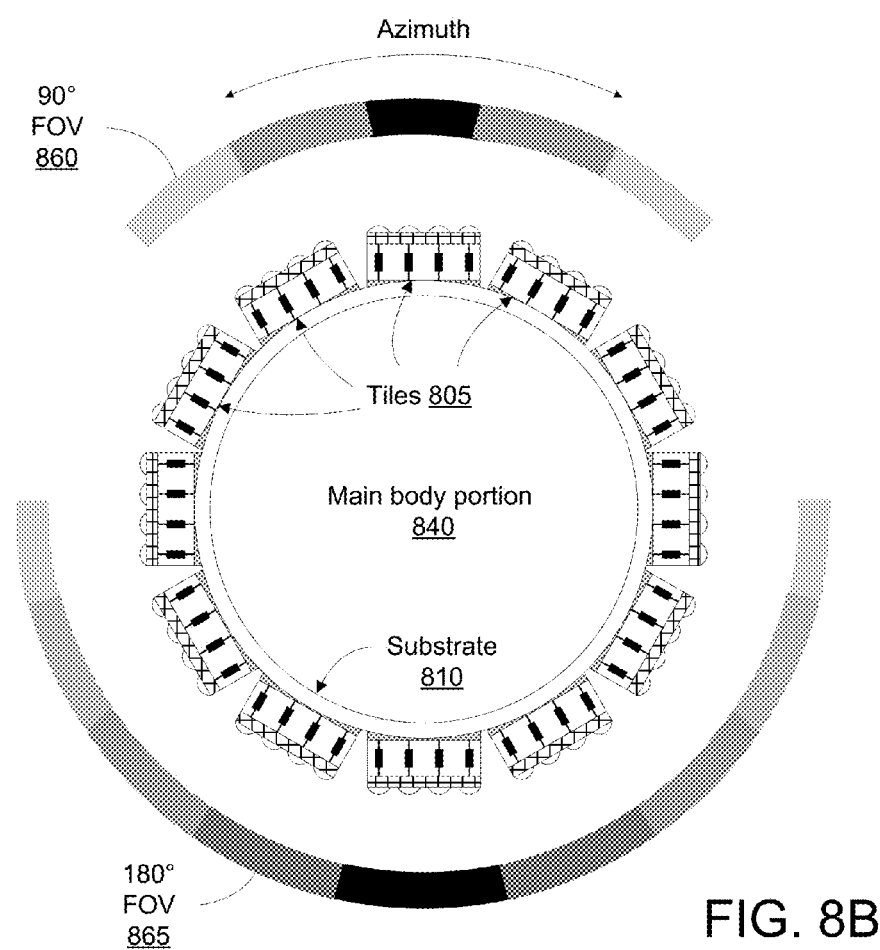

FIG. 8A illustrates an example of a probe device 800, according to an embodiment, that comprises a plurality of tiles disposed on a flexible substrate. A cross-sectional view of probe device 800 is shown in FIG. 8B. As shown in FIG. 8A, probe device 800 may include a main body portion 840 having a distal end 830, where curved sides are formed along the length of main body portion 840. Multiple tiles 805 of probe device 800 may be variously located along such curved sides of main body portion 840 and, in an embodiment, may variously face radially away from main body portion 840. Accordingly, the transducer membrane structures of tiles 805 may be variously operated each to send a pressure wave in a direction which its respective tile faces. Some or all of tiles 805 may each have one or more features of tile 300, for example.

Although certain embodiments are not limited in this regard, tiles 805 may each be coupled to a flexible substrate 810 which, for example, has some or all of the features of substrate 610 (or substrate 710). For example, tiles 805 may be arranged in an array on substrate 810, as represented by the illustrative 8×2 array shown for probe 800. Substrate 810 may conform and couple to a curved side of main body portion 840. In one embodiment, substrate 810 extends around a circumference (or other perimeter) of main body portion 840.

Substrate 810 may have disposed therein or thereon signal lines—as represented by the illustrative signal lines 815—to variously couple tiles 805 to one another and/or to an interface (not shown) for substrate 810 to exchange control, data and/or other signals. For example, such an interface may provide for signal exchanges between substrate 810 and one or more interconnects 850 which are to couple probe device to some remote system (not shown). In one embodiment, such exchanges are via a compatibility circuit (not shown) which, for example, may be located within distal end 830. The compatibility circuit may be programmable to provide signal processing for communication between probe device 800 and a particular type of remote system.

As shown in FIG. 8B, selective activation of transducer elements of tiles 805 may provide for probe device 800 to generate any of a wide variety of propagating ultrasonic waves. For example, various transducer elements may be activated along a line extending in a direction (referred to herein as "elevation") along the length of main body portion 840. Such activation may facilitate the generation of image information which represents an image slice along the elevation direction. As shown in view 870, different groups of transducer elements may be successively activated over time to provide for movement of such a slice along the elevation of main body portion 840 and/or around a periphery (or "azimuth") of main body portion 840.

Alternatively or in addition, transducer elements may be activated along the periphery of main body portion 840 to facilitate the generation of other image information which represents an image slice around at least a portion of the periphery. In an embodiment, a range of transducer elements may be chosen for a particular field of view (FOV), as variously represented by the illustrative 90° FOV 860 and 180° FOV 865. As shown in view 872, different groups of transducer elements may be successively activated over time to provide for movement of such an azimuthal slice along the elevation and/or around the periphery of main body portion 840.

In some embodiments, activation of transducer elements of tiles 805 may vary not only with respect to time, but voltage, duration, frequency and/or the like. Based on such variation, multiple ones of the tiles 805 may operate in concert to implement a curved linear or planar phased array. In the example represented by FIG. 8B, 90° FOV 860 and 180° FOV 865 are variously characterized each by a respective gradient based on their various azimuthal positions. Such a gradient may be for an amplitude, frequency, duration, delay or other characteristic of a propagating wave generated by tiles 805. As shown in view 874, different groups of transducer elements may be successively activated over time to provide for movement of a phased array along the elevation and/or around the periphery of main body portion 840.

Selective activation of the different groups of transducer elements may provide for imaging of a tapered volume—e.g. including the illustrative wedge-shaped volume 876—which extends as a projection from the surface of the probe. The volume to be imaged and/or the type of imaging to be performed for the volume may be changed by successively reconfiguring whether and/or how transducer elements are to be activated at certain regions of main body portion 840. For example, movement of the phased array along the elevation and/or around the periphery of main body portion 840 may result in corresponding movement of the imaged volume 876 along or around main body portion 840.

For certain applications, a probe device may include base structures which are variously positioned around a tightly curved surface of the probe device, where such base structures each support a respective plurality of transducer elements. However, for each such base structures, a surface of the base structure for supporting the respective transducer elements may be relatively flat—e.g. as compared to a radius of curvature (ROC) of the surface on which the base is disposed. The various orientations of these flat transducer elements may not be conducive to beam steering or propagation of smoothly curving waves in a medium.

Figure 9A:
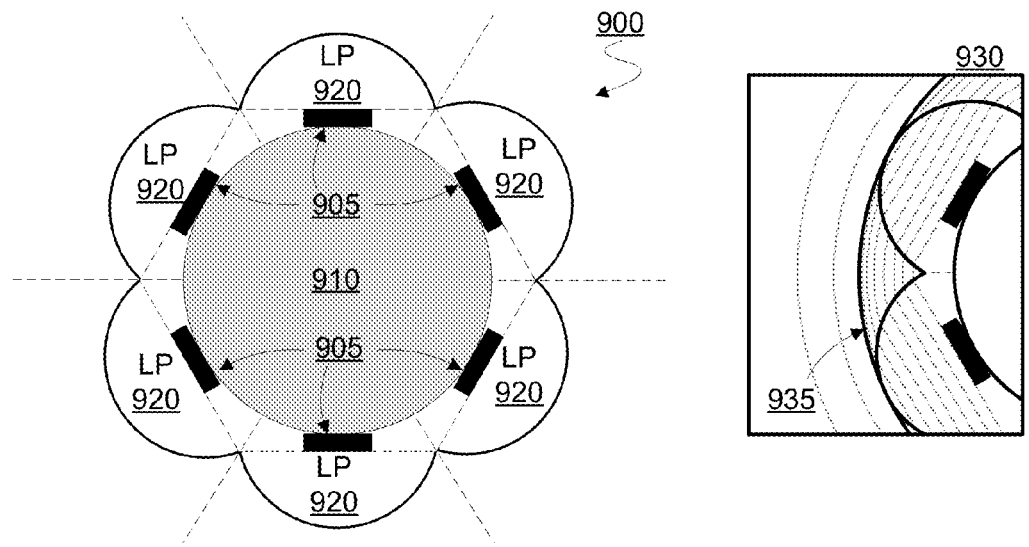
FIGS. 9A, 9B are functional block diagrams illustrating elements of respective lens structures each according to a corresponding embodiment.

For example, FIG. 9A shows a cross-sectional view of a probe device 900 including tiles 905 variously disposed around a main body portion 910. Tiles 905 may be coupled to main body portion 910 via a flexible substrate (not shown) such as substrate 610, for example, although certain embodiments are not limited in this regard. In the cross-section of probe device 900, transducer elements (not shown) on the respective outward-facing surfaces of tiles 905 may conform to a polygonal or otherwise piecewise continuous geometry. However, it is often desirable for a circular, elliptical or other smoothly curved wave front to propagate from devices such as probe device 900.

To facilitate propagation of comparatively smoother waves, certain embodiments provide one or more curved lens structures which are variously disposed each around or over a respective planar array of transducer elements. By way of illustration and not limitation, probe device 900 further comprises a respective convex lens portion (LP) 920 for each of multiple tiles 905 positioned around main body portion 910. For some or all of the LPs 920, a cross-sectional profile of the LP 920 may conform at least in part to a semicircular, semielliptical, parabolic or other curved shape.

The shape of a LP 920 may facilitate applications wherein a speed $C_{lens}$ of an ultrasound wave through LP 920 is greater than a speed $C_{media}$ of an ultrasound wave through a media surrounding, adjacent or otherwise proximate to LP 920. For example, where an adjoining media is predominantly comprised of water (as in various medical diagnostic applications), LP 920 may include any of various epoxy encapsulant materials such as Stycast® 1090SI from Emerson & Cuming. However, any of a variety of alternative materials may be used to form some or all LP 920, according to implementation-specific details.

As shown in view 930, as successive waves from tiles 905 propagate each through a respective convex LP 920, the edges of such waves may begin to lag after they enter into a media having slower sound propagation characteristics. Although certain embodiments are not limited in this regard, device 900 may further comprise a sheathing material 935 which has such slower sound propagation characteristics. By the time a given wave leaves its respective convex LP 920, the overall wave front has a comparatively smooth curved (e.g. arc) shape.

Figure 9B:
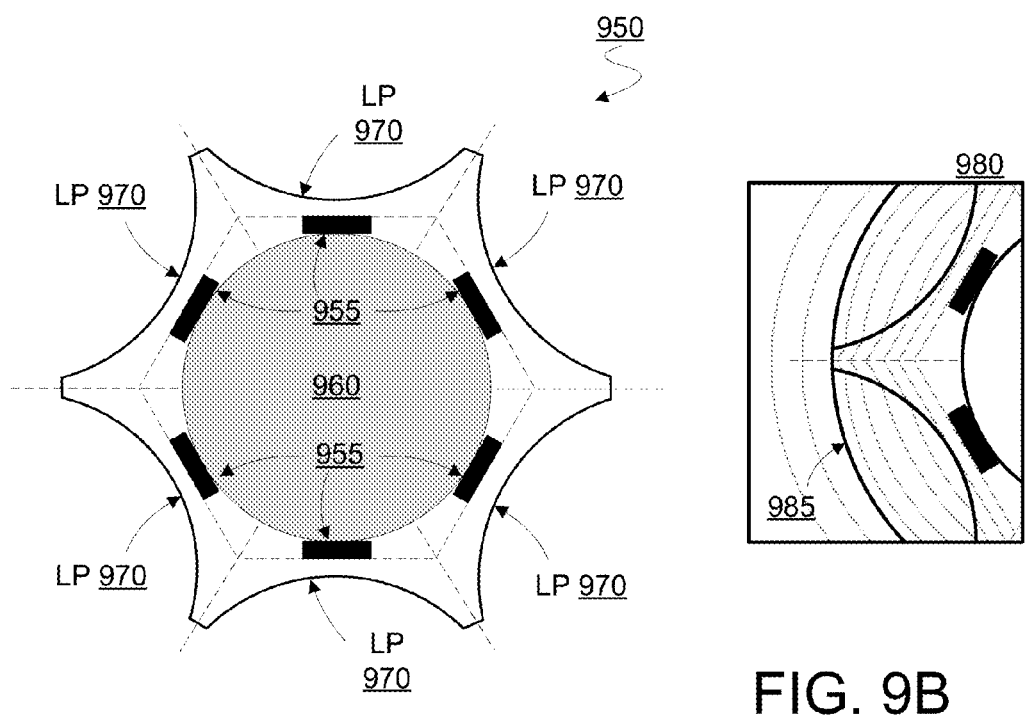

FIG. 9B shows a cross-sectional view of another probe device 950 comprising tiles 955 variously positioned around a tightly curved surface of a main body portion 960. In the illustrative embodiment of probe device 950, one or more concave LPs 970 may each be disposed around or over a respective one of tiles 905. For some or all of the LPs 970, a cross-sectional profile of the LP 970 may conform at least in part to a semicircular, semielliptical, parabolic or other curved shape. The shape of a LP 970 may facilitate applications wherein $C_{lens}$ for LP 970 is less than $C_{media}$ for a media surrounding, adjacent or otherwise proximate to LP 970. For example, where an adjoining media is predominantly comprised of water, LP 920 may include any of various types of room temperature vulcanizing (RTV) silicone rubber. However, any of a variety of alternative materials may be used to form some or all LP 920, according to implementation-specific details.

As shown in view 980, as successive waves from tiles 955 propagate each through a respective concave LP 970, the middle of such waves may begin to lead the edges of the wave after they enter into a media having faster sound propagation characteristics. Although certain embodiments are not limited in this regard, device 950 may further comprise a sheathing material 985 which has such faster sound propagation characteristics. By the time a given wave leaves its respective concave LP 970, the overall wave front has a comparatively smooth curved shape.

Figure 10:
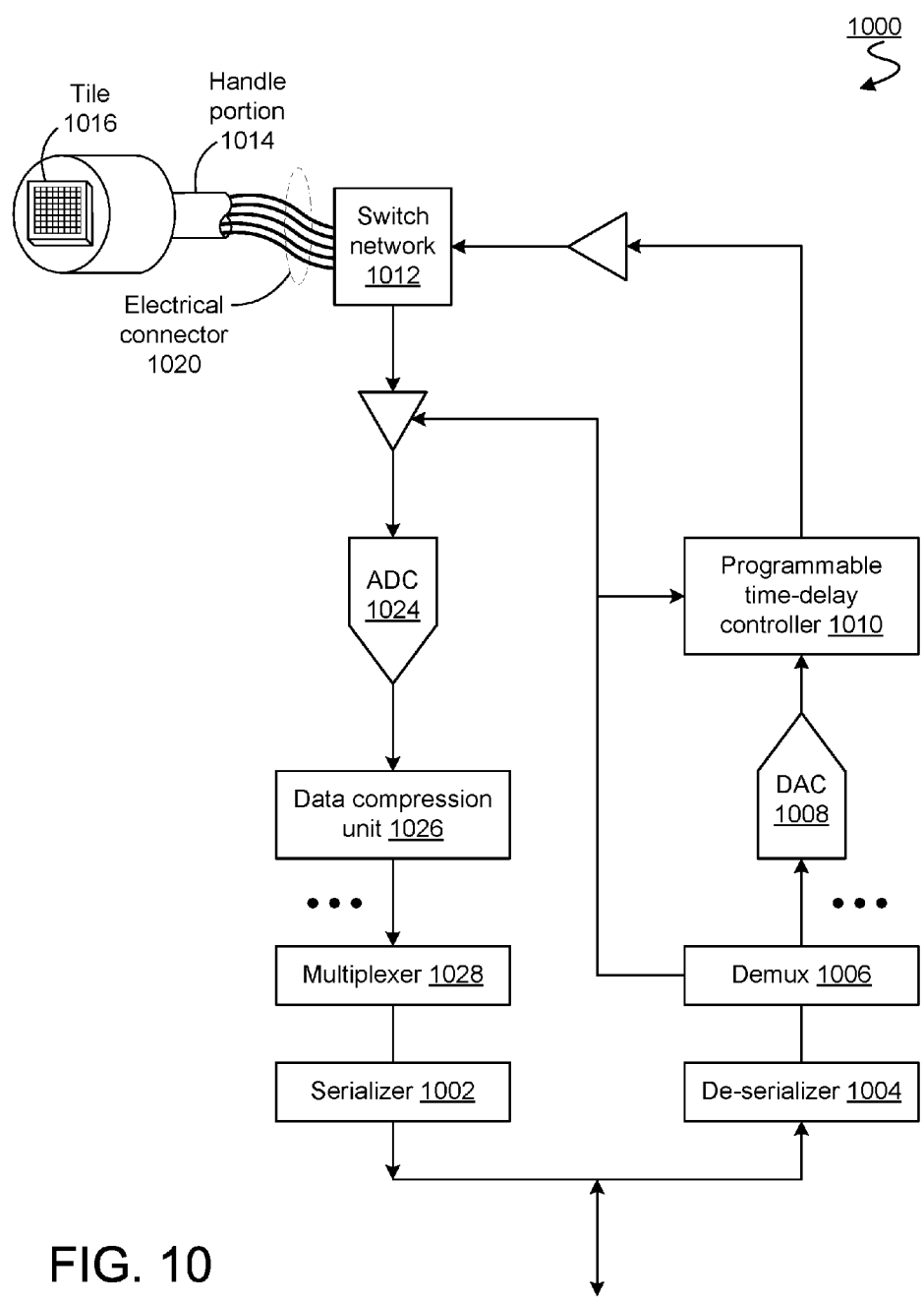
FIG. 10 is a functional block diagram illustrating elements of an ultrasonic transducer system according to an embodiment.

FIG. 10 is a functional block diagram of an ultrasonic transducer apparatus 1000 that employs a transducer device, in accordance with an embodiment. In an exemplary embodiment, the ultrasonic transducer apparatus 1000 is for generating and sensing pressure waves in a medium, such as water, tissue matter, etc. The ultrasonic transducer apparatus 1000 has many applications in which imaging of internal structural variations within a medium or multiple media is of interest, such as in medical diagnostics, product defect detection, etc. The apparatus 1000 includes at least one tile 1016 (and, in an embodiment, flexible substrate and/or lens structures), which may include structures and mechanisms described elsewhere herein. In exemplary embodiment, the tile 1016 is housed in a handle portion 1014 which may be manipulated by machine or by a user of the apparatus 1000 to change the facing direction and location of an active surface of tile 1016 as desired (e.g., facing the area(s) to be imaged). Electrical connector 1020 electrically couples drive/sense electrodes of tile 1016 to a communication interface external to the handle portion 1014.

In embodiments, the apparatus 1000 includes at least one signal generator, which may be any known in the art for such purposes, coupled to tile 1016, for example by way of electrical connector 1020. The signal generator is to provide an electrical signal to indicate a trigger event for driving various drive/sense electrodes. In an embodiment, one or more signal generators each includes a de-serializer 1004 to de-serialize control signals that are then de-multiplexed by demux 1006. The exemplary signal generator further includes a digital-to-analog converter (DAC) 1008 to convert the digital control signals into signals for triggering activation of individual transducer elements in tile 1016. Respective time delays can be added to the individual drive voltage signal by a programmable time-delay controller 1010 to beam steer, create the desired beam shape, focus, and direction, etc. Coupled between the pMUT channel connector 1020 and the signal generator is a switch network 1012 to switch tile 1016 between drive and sense modes.

In embodiments, the apparatus 1000 includes at least one signal receiver, which may be any known in the art for such purposes, coupled to tile 1016, for example by way of electrical connector 1020. The signal receiver(s) is to collect an electrical response signal from each the drive/sense electrode channels in tile 1016. In one exemplary embodiment of a signal receiver, an analog to digital converter (ADC) 1024 is to receive voltages signals and convert them to digital signals. The digital signals may then be stored to a memory (not depicted) or first passed to a signal processor. An exemplary signal processor includes a data compression unit 1026 to compress the digital signals. A multiplexer 1028 and a serializer 1002 may further process the received signals before relaying them to a memory, other storage, or a downstream processor, such as an image processor that is to generate a graphical display based on the received signals.

Techniques and architectures for operating a piezoelectric transducer device are described herein. In the above description, for purposes of explanation, numerous specific details are set forth in order to provide a thorough understanding of certain embodiments. It will be apparent, however, to one skilled in the art that certain embodiments can be practiced without these specific details. In other instances, structures and devices are shown in block diagram form in order to avoid obscuring the description.

Reference in the specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

Some portions of the detailed description herein are presented in terms of algorithms and symbolic representations of operations on data bits within a computer memory. These algorithmic descriptions and representations are the means used by those skilled in the computing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the discussion herein, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Certain embodiments also relate to apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs) such as dynamic RAM (DRAM), EPROMs, EEPROMs, magnetic or optical cards, or any type of media suitable for storing electronic instructions, and coupled to a computer system bus.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description herein. In addition, certain embodiments are not described with reference to any particular programming language. It will be appreciated that a variety of programming languages may be used to implement the teachings of such embodiments as described herein.

Besides what is described herein, various modifications may be made to the disclosed embodiments and implementations thereof without departing from their scope. Therefore, the illustrations and examples herein should be construed in an illustrative, and not a restrictive sense. The scope of the invention should be measured solely by reference to the claims that follow.

What is claimed is:

1. A probe device comprising:
    a main body portion including a convex surface formed in a cross-sectional plane which extends through the probe device;
    a plurality of tiles each coupled to the main body portion via the convex surface, wherein, in the cross-sectional plane, the plurality of tiles are distributed around the main body portion, the plurality of tiles each including:
        a plurality of microelectromechanical piezoelectric transducer elements; and
        a base including a first flat side adjoining and supporting the plurality of microelectromechanical piezoelectric transducer elements, wherein the first flat side faces away from the convex surface; and
    a lens structure which extends around the main body portion in the cross-sectional plane, the lens structure including curved lens portions each coupled to a respective one of the plurality of tiles, wherein, in the cross-sectional plane, the curved lens portions are distributed around the main body portion and each of the curved lens portions adjoins a respective other of the curved lens portions, wherein, for each tile of the plurality of tiles, the plurality of microelectromechanical piezoelectric transducer elements of the tile are to propagate a wave away from the convex surface and toward the respective curved lens portion;
    wherein, for each of the curved lens portions, a concavity of the lens portion or a convexity of the lens portion ends in a region between the respective tile and a corresponding other tile closest to the respective tile.

2. The probe device of claim 1, wherein the curved lens portions include multiple distinct concave lens portions.

3. The probe device of claim 2, wherein the multiple distinct concave lens portions comprise a room temperature vulcanizing (RTV) silicone rubber.

4. The probe device of claim 1, wherein the curved lens portions include multiple distinct convex lens portions.

5. The probe device of claim 4, wherein the multiple distinct convex lens portions comprise an epoxy encapsulant material.

6. The probe device of claim 1, further comprising a sheath material surrounding the curved lens portions.

7. The probe device of claim 1, wherein for one of the curved lens portions, a cross-sectional profile of the lens portion conforms to one of a circular shape, an elliptical shape and a parabolic shape.

8. The probe device of claim 1, wherein the curved lens portions are contiguous with one another.

9. The probe device of claim 1, further comprising a frame coupling the lens portions to one another and to a shaft of the probe.

10. The probe device of claim 1, further comprising a flexible substrate extending around a periphery of the main body portion, wherein the plurality of tiles are coupled to the main body portion via the flexible substrate.

11. A system comprising:
 a probe device of any of claims 1 through 10;
 receiving means coupled to the probe device to receive electrical response signals from the probe device; and
 signal processing means coupled to the receiving means to process the electrical response signals received from the probe device.

* * * * *